United States Patent
Chung et al.

(10) Patent No.: US 11,110,450 B2
(45) Date of Patent: Sep. 7, 2021

(54) SAMPLE-REAGENT MIXTURE THERMAL CYCLING

(71) Applicant: HEWLETT-PACKARD DEVELOPMENT COMPANY, L.P., Houston, TX (US)

(72) Inventors: Bradley D. Chung, Corvallis, OR (US); Alexander N. Govyadinov, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 700 days.

(21) Appl. No.: 15/749,077

(22) PCT Filed: Jan. 29, 2016

(86) PCT No.: PCT/US2016/015640
§ 371 (c)(1),
(2) Date: Jan. 30, 2018

(87) PCT Pub. No.: WO2017/131740
PCT Pub. Date: Aug. 3, 2017

(65) Prior Publication Data
US 2018/0229230 A1 Aug. 16, 2018

(51) Int. Cl.
*B01L 3/02* (2006.01)
*B01L 7/00* (2006.01)
*C12Q 1/686* (2018.01)
*B25J 9/02* (2006.01)
*B01L 3/00* (2006.01)

(52) U.S. Cl.
CPC .............. *B01L 3/0268* (2013.01); *B01L 7/52* (2013.01); *B25J 9/026* (2013.01); *B01L 3/5088* (2013.01); *B01L 2300/0819* (2013.01); *B01L 2300/185* (2013.01); *B01L 2300/1827* (2013.01); *B01L 2300/1838* (2013.01); *B01L 2300/1894* (2013.01); *C12Q 1/686* (2013.01)

(58) Field of Classification Search
None
See application file for complete search history.

(56) References Cited

U.S. PATENT DOCUMENTS 6,225,061 B1 * 5/2001 Becker ...................... B01J 19/16
506/16
6,533,255 B1    3/2003 Mitsuhashi et al.
6,615,914 B1    9/2003 Young
(Continued)

FOREIGN PATENT DOCUMENTS

KR    10-20140134435 A    11/2014
WO    WO-2013139970 A1    9/2013

OTHER PUBLICATIONS

Fuchiwaki, Y. et al.; "Study of a Liquid Plug-flow Thermal Cycling Technique Using a Temperature Gradient-based Actuator"; http://www.ncbi.nlm.nih.gov/pubmed/25350508; Oct. 27, 2014.
(Continued)

*Primary Examiner* — William H. Beisner
(74) *Attorney, Agent, or Firm* — Perry + Currier Inc (57) ABSTRACT

A sample-reagent mixture is thermal cycled through a plurality of cycles. Each thermal cycle includes actuating a heater to heat the sample-reagent mixtures; and dispensing a fluid onto the sample-reagent mixture to cool the sample reagent mixture.

14 Claims, 8 Drawing Sheets

(56) References Cited

U.S. PATENT DOCUMENTS

| | | |
|---|---|---|
| 6,633,785 B1 | 10/2003 | Kasahara et al. |
| 6,916,113 B2 | 7/2005 | Van de Goor et al. |
| 7,787,117 B1 | 8/2010 | Leona et al. |
| 2001/0039014 A1 | 11/2001 | Bass et al. |
| 2003/0138829 A1 | 7/2003 | Unger et al. |
| 2005/0205136 A1 | 9/2005 | Freeman et al. |
| 2006/0107769 A1 | 5/2006 | Emoto |
| 2008/0006653 A1 | 1/2008 | Dai et al. |
| 2009/0203082 A1 | 8/2009 | Schlaubitz et al. |
| 2010/0297640 A1 | 11/2010 | Kumar et al. |
| 2012/0002190 A1* | 1/2012 | Laitinen ............ G01N 21/6452 356/32 |
| 2012/0046203 A1 | 2/2012 | Walsh et al. |
| 2012/0075378 A1 | 3/2012 | Baldy et al. |
| 2013/0143272 A1 | 6/2013 | Guo et al. |
| 2014/0028995 A1 | 1/2014 | Bratkovski et al. |
| 2014/0051159 A1 | 2/2014 | Bergstedt et al. |
| 2015/0116706 A1 | 4/2015 | Barcelo et al. |

OTHER PUBLICATIONS

Choi, Sun et al., "A Zero-power, High-throughput Micro, Nanoparticle Printing via Gravity-driven Formation of Picoliter-scale Droplets" Oct. 2-6, 2011. http://www.rsc.org/images/LOC/2011/PDFs/Papers/595_1015.pdf.

Rajapandiyan, Panneerselvam et al. "Sensitive cylindrical SERS substrate array for rapid microanalysis of nucleobases." Analytical chemistry 84.23 (Nov. 2012): 10277-10282.

* cited by examiner

| STEP | TEMP | TIME [1] |
|---|---|---|
| DENATURE [2] | 94-98C | <.01s |
| ANNEAL [3] | 50-65C | |
| EXTEND [3] (500BP) | 75-80C | 3.1s |

SAMPLE-REAGENT MIXTURE THERMAL CYCLING

BACKGROUND

Thermal cycling involves cycles of repeated heating and cooling of a solution. Thermal cycling is often used in polymerase chain reaction technology to replicate copies of a particular DNA sequence. The polymerase chain reaction process is often labor intensive and the thermal cycling part of the process is particularly time-consuming.

DETAILED DESCRIPTION OF EXAMPLES

Figure 1:
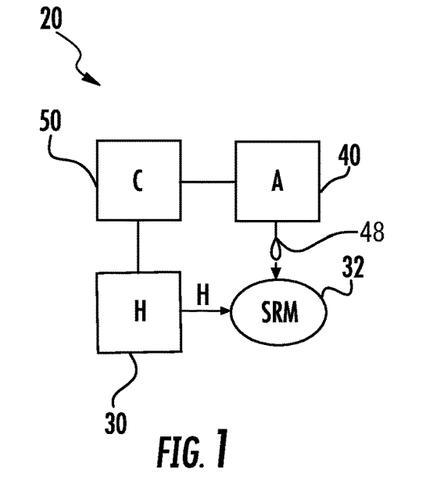
FIG. 1 is a schematic diagram of an example thermal cycling system.

FIG. 1 schematically illustrates an example thermal cycling system 20. Thermal cycling system 20 may be used to repeatedly heat and cool a solution. In one implementation, thermal cycling system 20 may be utilized to facilitate a polymerase chain reaction, a molecular biology technology used to amplify a single copy or a few copies of a piece of DNA across several orders of magnitude to generate thousands to millions of copies of the particular DNA sequence. Polymerase chain reactions utilize thermal cycling, wherein each cycle includes a denaturing step in which the solution is heated to an elevated temperature (for example, 94 degrees Celsius to 98 degrees Celsius), an annealing step in which the solution is cooled to a lower temperature (for example, 50 degrees Celsius to 65 degrees Celsius) and an extension/elongation step in which the solution is maintained at a temperature between the elevated temperature and the lower temperature (for example, 70 degrees Celsius to 80 degrees Celsius depending upon the DNA polymerase being used). Some polymerase chain reactions additionally comprise an initiation step in the first cycle, a final elongation step during the last cycle and a final hold step if short-term storage is desired.

Thermal cycling system 20 may facilitate compact, lower-cost and faster thermal cycling as compared to existing thermal cycling systems which often are large, complex and expensive and which take relatively long periods of time to carry out such thermal cycling. As will be described hereafter, thermal cycling system 20 carries out cycling by repeatedly heating and cooling a solution or sample-reagent mixture, wherein the cooling portion of each cycle is achieved through the dispensing of additional fluid, such as additional reagent, onto the previously heated solution or mixture.

As illustrated by FIG. 1, thermal cycling system 20 comprises heater 30, applicator 40 and controller 50. Heater 30 comprises a device that applies heat (H) to a sample-reagent mixture (SRM) 32. In one implementation, heater 30 comprises a resistor through which electrical current is supplied to generate heat that is conducted or otherwise directed to SRM 32. In other implementations, heater 30 may comprise a device that generates or emits heat in other fashions. In one implementation, heater 30 is part of a heating platform or other heating support upon which or in which an SRM support is removably or releasably placed for heating the SRM during a cycle or multiple cycles during thermal cycling. For this disclosure, the term "releasably" or "removably" with respect to two structures, means that the two structures may be repeatedly connected and disconnected to and from one another without material damage to either structure. In one implementation, heater 30 is embedded within or otherwise incorporated as part of the SRM support, below the surface of the support supporting the SRM 32, such that the heater 30 is carried with the SRM support along with the SRM 32. In another implementation, heater 30 radiates or otherwise directs heat from above and towards the SRM 32 carried by the underlying SRM support.

Applicator 40 comprises a device that dispenses a fluid onto SRM 32, wherein the fluid is at a temperature lower than the temperature of the SRM 32 at the time that the SRM 32 is to receive the fluid. In one implementation, applicator 40 comprises an onboard fluid supply, such as a cartridge or chamber. In one implementation, applicator 40 comprises a remote fluid supply, wherein the fluid supplies remote from the dispensing locations of applicator 40. In some implementations, applicator 40 comprises multiple distinct fluid supplies or sources containing different fluids or the same fluid but at different temperatures, wherein applicator 40 selectively applies each of the different fluids. For example, in one implementation, applicator 40 may apply a first fluid at a first time and a second different fluid (either differing in composition and/or differing in temperature) at a second different time.

In one implementation, applicator 40 dispenses fluid, such as additional reagent, at a temperature of less than or equal to 40 degrees Celsius. In one implementation, applicator 40 comprises an automated droplet dispenser that dispenses droplets 48 of the fluid, under power, in response to control signals from controller 50. In one implementation, applicator 40 forcefully dispenses the drops 48 of fluid, such as by jetting the drops of fluid, wherein the forcefully dispensed drops of the fluid additionally stir or mix SRM 32. In one implementation, applicator 40 comprises a piezo resistive firing element, wherein electrical current causes deflection of a diaphragm or membrane to forcefully expel the fluid through a nozzle or other opening. In another implementation, applicator 40 comprises a thermal resistive or bubble jet firing element, wherein electrical current is directed across a resistor to vaporize adjacent fluid and create a bubble that forcefully expels adjacent fluid through nozzle or other opening. In one implementation, applicator 40 comprises a bubble jet print head. In yet other implementations, applicator 40 comprises other fluid ejection or controlled volume fluid dispensing devices.

Controller 50 comprises a device that controls heater 30 and applicator 40 to thermal cycle SRM 32. In one implementation, controller 50 comprises a processing unit that follows instructions contained in a non-transitory computer-readable medium, wherein controller 50 outputs control signals that command heater 30 and applicator 40 to thermal cycle SRM 32. In one implementation, during each cycle of multiple cycles, controller outputs control signals actuating heater 30 to heat SRM 32 and also outputs control signals actuating applicator 40 to dispense a fluid onto SRM 32 to cool SRM 32. As a result, during a cycle, SRM 32 is heated and cooled.

For purposes of this application, the term "processing unit" shall mean presently developed or future developed processing hardware that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 50 may be embodied as part of one or more application-specific integrated circuits (ASICs). Unless otherwise specifically noted, the controller is not limited to any specific combination of hardware circuitry and software, nor to any particular source for the instructions executed by the processing unit.

Figure 2:
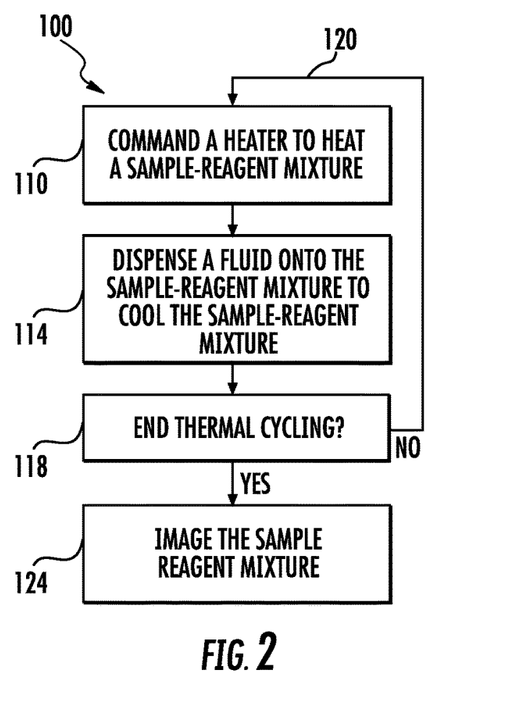
FIG. 2 is a flow diagram of an example thermal cycling method.

FIG. 2 is a flow diagram illustrating an example thermal cycling method 100 that may be carried out by system 20 or any of the thermal cycling system described hereafter. For purposes of explanation, method 100 will be described as being carried out by system 20. As indicated by block 110, controller 50 outputs control signals to command heater 30 to heat the sample reagent mixture, SRM 32. In one implementation in which such thermal cycling is utilized for a polymerase chain reaction, SRM 32 is heated and maintained at a temperature to facilitate denaturing of SRM 32 during each cycle. In one implementation, SRM 32 is heated to and maintained at a temperature of at least 90 degrees Celsius and nominally a temperature of 94 degrees Celsius to 98 degrees Celsius for a time period of less than or equal to 0.02 seconds and nominally less than or equal to 0.01 seconds during each cycle.

As indicated by block 114, controller 50 outputs control signals to command applicator 40 to dispense a fluid, such as a supplemental or additional reagent, onto SRM 32 so as to cool SRM 32. In one implementation where the thermal cycling method 100 is employed as part of a polymerase chain reaction, controller 50 causes applicator 40 to dispense a fluid at a temperature or multiple temperatures and of sufficient total volume to cool or lower the temperature of SRM to facilitate annealing during an individual cycle. The applied fluid quickly and effectively cools SRM 32. In some implementations, the additional fluid applied during each cycle further replenishes fluid in SRM 32 but may have been lost to evaporation. In some implementations, SRM 32 has an outer coating or covering of oil or other fluid to inhibit or reduce such evaporation. In one implementation, the relative volume and temperature of the SRM 32 and the volume, temperature and number of the droplets of fluid dispensed onto the SRM 32 are such that SRM 32 experiences a temperature drop from 94 degrees Celsius to 98 degrees Celsius down to 50 degrees Celsius to 65 degrees Celsius. In one implementation, the temperature drop occurs during a time period of no greater than 2 seconds and, in one particular implementation, no greater than 0.5 seconds.

In one implementation, a single droplet of fluid is dispensed onto SRM 32 during each cycle. In another implementation, multiple droplets of fluid are dispensed onto SRM 32 during each cycle. In one implementation, the fluid being dispensed is at a temperature of less than or equal to 40 degrees Celsius. In implementations where multiple droplets are dispensed during a cycle, the temperature of each of the droplets is uniform or the same. In other implementations, the temperature of each of the drop is dispensed during a single cycle may be controlled so as to vary with respect to one another during the individual cycle. In some implementations, the temperature of the drops dispensed may vary from cycle to cycle during the thermal cycling.

In one example implementation, SRM 32 has a volume of less than or equal to 200 pico liters. In one implementation, SRM 32 has a volume of 100 to 200 pico liters, and nominally from 160 pico liters to 170 pico liters. At the beginning of each cycle during thermal cycling, SRM 32 is at a temperature of at least 94 degrees Celsius to 98 degrees Celsius prior to receiving a droplet or multiple droplets of fluid from applicator 40. In such an implementation, controller 50 outputs control signals such that actuator 40, a bubble jet fluid dispenser, jets or otherwise dispenses five droplets onto SRM 32, each of the droplets of the fluid having a temperature less than the temperature of SRM 32. In one implementation, each of the droplets is at a uniform temperature of between 35 and 40 degrees Celsius. In one implementation, each droplet has a volume of between 20 and 40 pico liters, and nominally 30 pico liters.

As indicated by block 118 and arrow 120, blocks 110 and block 114 are repeatedly carried out or cycled during thermal cycling until a predetermined threshold or a predetermined number of cycles have been achieved. In one implementation, each cycle has a duration of less than or equal to six seconds. For example, in one implementation where method 100 is carried out as part of a polymerase chain reaction involving denaturing, annealing and extending steps during each cycle, denaturing may consume less than or equal to two seconds, and in some implementations, less than or equal to 0.01 seconds. Annealing and extending may consume less than or equal to five seconds, in some implementations, less than or equal to 3.5 seconds.

In one implementation, thermal cycling method 100 comprises at least 25 cycles, and in one implementation, at least 30 cycles. In one implementation, method 100 comprises the completion of at least 30 cycles in less than or equal to a total time of two minutes. In one implementation, method 100 completes 30 cycles in less than or equal to 1.6 minutes.

As indicated by block 124, upon completion of thermal cycling, SRM 32 is imaged. In one implementation, SRM 32 is relocated to opposite to a camera. In another implementation, a camera is positioned opposite to SRM. The images of SRM 32 are analyzed to identify characteristics of SRM 32.

Figure 3:
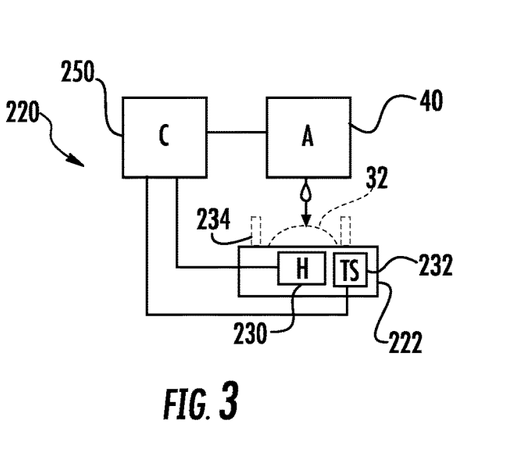
FIG. 3 is a schematic diagram of another example thermal cycling system.

FIG. 3 schematically illustrates thermal cycling system 220, an example implementation of thermal cycling system 20. Thermal cycling system 220 comprises SRM support 222, heater 230 and temperature sensor 232, applicator 40 (described above) and controller 250. SRM support 222 comprises a platform or carrier upon which SRM 32 rests or is contained during thermal cycling. In one implementation, SRM support 222 comprises a plate which underlies SRM 32 during thermal cycling. In yet another implementation, SRM support 222 comprises a chamber or well which underlies and extends along sides of SRM 32 during thermal cycling. For example, as shown in broken lines in FIG. 3, in one implementation, support 222 may comprise sidewalls 234. Such sidewalls 234 may serve to reduce expansion of SRM 32 upon the upper surface of support 222, facilitating taller columns of SRM 32 to reduce the surface area occupied by a single SRM 32. Although SRM support 22 is illustrated as supporting a single SRM 32, in other implementations, SRM support 222 may be scaled or enlarged so as to support a row, pattern, layout or two-dimensional array of SRMs 32 at discrete spaced locations on the upper surface of SRM support 222.

Heater 230 is similar to heater 30 described above except that heater 230 is connected to or otherwise provided as part of support 222 so as to be carried or moved with support 222. In the example illustrated, heater 230 is embedded or otherwise incorporated into the structure forming support 222. Heater 230 is located sufficiently proximate to the upper surface of support 222 so as to generate and apply heat to SRM 32 during thermal cycling. In one implementation, heater 230 comprises an electrical resistor that generator emits heat in response to electrical current flowing through the resistor. In other implementations, heater 230 may comprise other heat generating and emitting devices.

Temperature sensor 232 comprises a temperature sensing device that outputs signals indicating or corresponding to a current temperature of SRM 32. In one implementation, temperature sensor 232 may comprise a temperature sensing diode. In yet other implementations, temperature sensor 232 may comprise other temperature sensing technologies or components. As further shown by FIG. 3, temperature sensor 232, like heater 230, is connected to or otherwise provided as part of support 222 so as to be carried or moved with support in 222. In the example illustrated, heater 230 is embedded or otherwise incorporated into the structure forming support 222.

Controller 250 is similar to controller 50 described above except the controller 250 is specifically illustrated as receiving signals output by temperature sensor 232. Similar to controller 50, controller 250 may carry out thermal cycling method 100 described above. In the example illustrated, controller 250 utilizes the signals received from temperature sensor 232, indicating the temperature of SRM 32, to control the thermal cycling of SRM 32 upon support 222. For example, in response to receiving signals indicating SRM 32 at a particular temperature, controller 250 may adjust the operation of heater 230 to apply additional heat to SRM 32 to further elevate the temperature of SRM 32. Alternatively, if a temperature threshold for SRM 32 has been satisfied, as indicated by signals from sensor 232, controller 250 may halt the application of new heat by heater 230 or may slow the rate at which heater 230 applies heat to SRM 32 to maintain SRM 32 at the temperature threshold or within a predefined temperature range. At such time, controller 250 may start a clock or initiated countdown for controlling the duration in which SRM 32 is at the predefined temperature or within the predefined temperature range. If signals from temperature sensor 232 indicate that SRM 32 is at a temperature above a predefined temperature threshold, such as during the annealing step of thermal cycling where the temperature of SRM 32 is cooled, controller 250 may output control signals adjusting the operation of applicator 42 further cool SRM 32 through the application of fluid. For example, controller 250 may output control signals to lower the temperature of the fluid being applied by applicator 40, to increase the rate or frequency at which cooling fluid, such as droplets, is applied SRM 32 and/or to increase the volume of the individual droplets of cooling fluid applied to SRM 32. In yet other implementations, temperature sensor 232 may be omitted.

Figure 4:
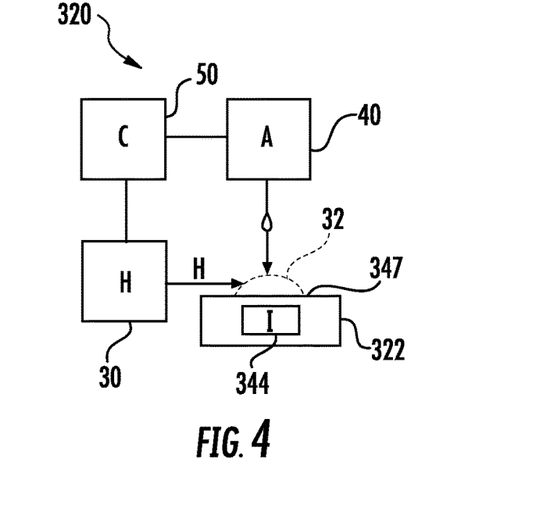
FIG. 4 is a schematic diagram of another example thermal cycling system.

FIG. 4 schematically illustrates thermal cycling system 320, another example implementation of thermal cycling system 20. Thermal cycling system 320 is similar to thermal cycling system 27 except that thermal cycling system 320 is illustrated as additionally comprising SRM support 322 and imager 344. Those components or elements of system 320 which correspond to elements or components of system 20 are numbered similarly.

SRM support 322 is similar to SRM support 222 except that SRM support 322 supports and carries imager 344. Imager 344 comprises a device to output signals based upon captured images of SRM 32 upon support from 322. In one implementation, imager 344 comprises a camera. Imager 344 is carried by support 22 facilitates imaging of SRM 32. In one implementation, imager 344 is contained within or embedded within support 322. In another implementation, imager 344 is positioned below support 322. In yet other implementations, imager 344 comprises additional optical focusing elements such as lenses or mirrors which direct or focus images SRM 32 to imager 344. In those implementations in which imager 344 is positioned below the uppermost surface 347 of support 322 or in which imager 344 receives images focused by a mirror or a lens below or opposite to surface 347, those portions of support 322 that are otherwise positioned between surface 347 supporting SRM 32 and imager 344 are transparent cassette images may be captured through such transparent surfaces. In yet other implementations, imager 344 may be supported to a side or above SRM 32 on surface 347.

Figure 5:
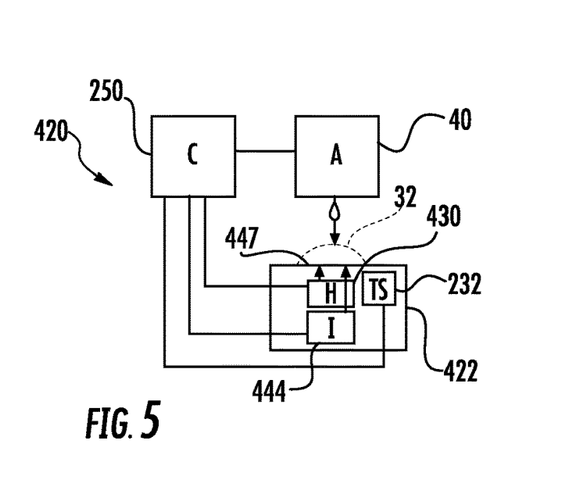
FIG. 5 is a schematic diagram of another example thermal cycling system.

FIG. 5 schematically illustrates thermal cycling system 420, another example implementation of thermal cycling system 20. Thermal cycling system 420 is similar to thermal cycling system 220 except that thermal cycling system 420 is specifically illustrated as comprising support 422, heater 430 and imager 444. Those remaining components of system 420 which correspond to components of system 220 are numbered similarly.

Support 422 is similar to support 322. In the example illustrated, support 422 overlies heater 430 and imager 444. Those portions of support 422 between heater 430 and the upper surface 447 supporting SRM 32 and those portions of support 422 between imager 444 and the upper surface 447 supporting SRM 32 are transparent or void such that imager 444 to capture images of SRM 32 on surface 447. For example, in one implementation, support 422 is formed from, or comprises, a transparent glass or a transparent substrate material.

Heater 430 is similar heater 230 except that heater 230 overlies imager 444 or is otherwise disposed between imager 444 and surface 447. For example, an image viewing path may extend from SRM 32 on surface 447 to imager 444, the image viewing path being angled or being redirected by a lens or mirror, wherein heater 430 intersects the image viewing path. In the example illustrated, heater 430 is transparent such as image viewing path may pass through heater 430. In one implementation, heater 430 comprises an electrically resistive heat generating element generates heat in response to being supplied with electrical current, wherein the electric resistor generating element is transparent. In one implementation, heater 430 is formed from, or comprises, a transparent indium tin oxide electrically conductive resistor element. In other implementations, other transparent heat generating elements may be utilized.

Imager 444 similar to imager 344 described above. As schematically illustrated in FIG. 5, imager 444 captures images of SRM 32 on support 422. Imager 444 capture such images using an image transmitting path, a path that allows the transmission of visible light, that passes through heater 430. In other implementations which imager 444 images SRM 32 using non-visible light or other wavelengths of light, both heater 430 and any intervening portions of support 420 are formed from, or comprises, material that facilitates transmission of the nonvisible light or other wavelengths of light.

Figure 6:
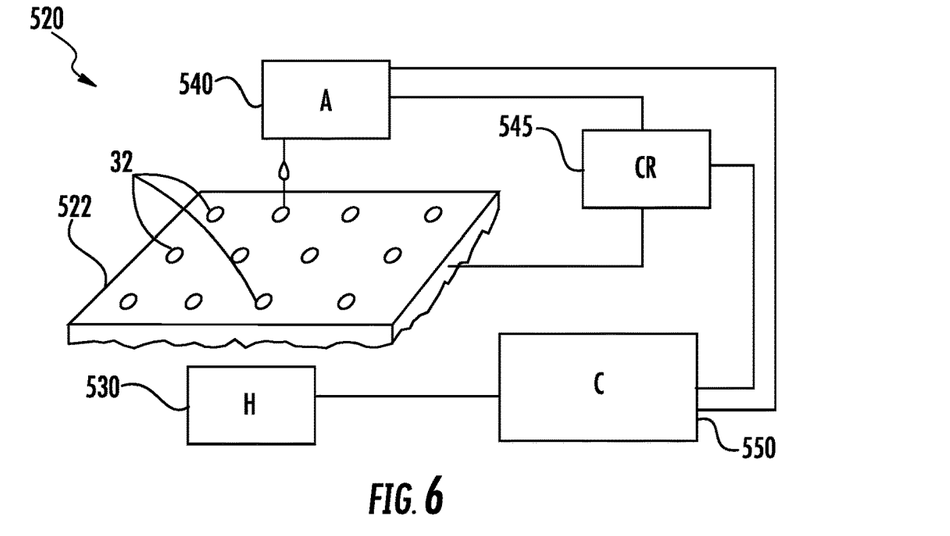
FIG. 6 is a schematic diagram of another example thermal cycling system.

FIG. 6 schematically illustrates thermal cycling system 520, another implementation of thermal cycling system 20. Thermal cycling system 520 facilitates large-scale thermal cycling. Thermal cycling system 520 comprises SRM support 522, heater 530, applicator 540, Cartesian robot 545 and controller 550. SRM support 522 comprises a plate which underlies distinct SRMs 32 during thermal cycling. In yet another implementation, SRM support 522 comprises a two-dimensional array, grid or other layout of multiple chambers or cells which underlie and extend along sides of SRMs 32 during thermal cycling.

Heater 530 is similar to heater 30 described in that heater 530 comprises a device that applies heat (H) to SRMs 32. In one implementation, heater 530 comprises a resistor through which electrical current is supplied to generate heat that is conducted or otherwise directed to SRMs 32. In other implementations, heater 530 may comprise a device that generates or emits heat in other fashions. In one implementation, heater 530 is part of a heating platform or other heating support upon which or in which an SRM support is removably or releasably placed for heating the SRM during a cycle or multiple cycles during thermal cycling. In one implementation, heater 530 is embedded within or otherwise incorporated as part of the SRM support, below the surface of the support supporting the SRMs 32, such that the heater 530 is carried with the SRM support along with the SRMs 32. In another implementation, heater 530 radiates or otherwise directs heat from above and towards the SRMs 32 carried by the underlying SRM support 522.

Applicator 540 comprises a device that dispenses a fluid onto SRMs 32, wherein the fluid is at a temperature lower than the temperature of the SRMs 32 at the time that the SRMs 32 are to receive the fluid. In one implementation, applicator 540 dispenses fluid, such as additional reagent, at a temperature of less than or equal to 40 degrees Celsius. In one implementation, applicator 540 comprises an automated droplet dispenser that dispenses droplets of the fluid, under power, in response to control signals from controller 550. In one implementation, applicator 540 forcefully dispenses the drops of fluid, such as by jetting the drops of fluid, wherein the forcefully dispensed drops of the fluid additionally stir or mix SRMs 32. In one implementation, applicator 540 comprises a piezo resistive firing element, wherein electrical current causes deflection of a diaphragm or membrane to forcefully expel the fluid through a nozzle or other opening. In another implementation, applicator 540 comprises a thermal resistive or bubble jet firing element, wherein electrical current is directed across a resistor to vaporize adjacent fluid and create a bubble that forcefully expels adjacent fluid through nozzle or other opening. In one implementation, applicator 40 comprises a bubble jet print head. In yet other implementations, applicator 40 comprise other fluid ejection or controlled volume fluid dispensing devices.

Cartesian robot 545, also sometimes referred to as an x-y scanning platform or a gantry robot, comprises a device that selectively repositions applicator 540 and/or SRM support 522 relative to one another. In one implementation, Cartesian robot 545 is operably coupled to applicator 540 to selectively reposition applicator 540 at each of a plurality of predefined locations with respect to SRM support 522, which may be stationary. In another implementation, Cartesian robot 545 is operably coupled to SRM support 522, either directly or indirectly, to selectively reposition support 522 at each of a plurality of predefined locations with respect to applicator 540, which may be stationary. In yet another implementation, Cartesian robot 545 is operably coupled to both applicator 540 and support 522 to selectively move and reposition each of applicator 540 and support 522 relative to one another. Cartesian robot 545 facilitates controlled positioning of applicator 540 such that fluid may be dispensed by applicator 540 at each of the plurality of distinct, discrete spaced locations of support 522 containing an individual SRM 32.

Controller 550 comprises a device that controls heater 530, applicator 540 and Cartesian robot 545 to thermal cycle SRMs 32. In one implementation, controller 550 comprises a processing unit that follows instructions contained in a non-transitory computer-readable medium, wherein controller 550 outputs control signals that command heater 530, applicator 540 and Cartesian robot 545 to thermal cycle SRMs 32. In one implementation, during each cycle of multiple cycles, controller outputs control signals actuating heater 530 to heat SRMs 32, outputs control signals actuating Cartesian robot 545 to appropriately position applicator 540, sequentially, with respect to each of the SRMs upon support 522 while also outputs control signals actuating applicator 540 to sequentially dispense a fluid onto each of SRMs 32 to cool each of SRMs 32. As a result, during a cycle, each of SRMs 32 is heated and cooled.

Figure 7:
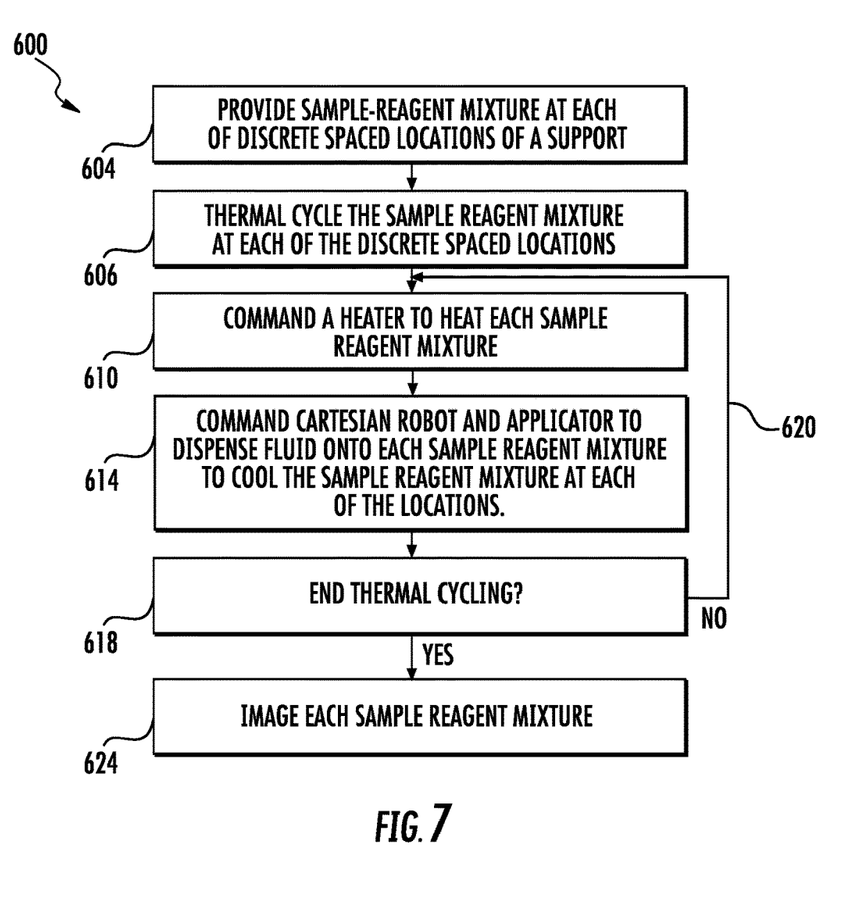
FIG. 7 is a flow diagram of an example thermal cycling method.

FIG. 7 is a flow diagram illustrating an example thermal cycling method 600. For purposes of explanation, method 600 will be described as being carried out by system 520 described above. As indicated by block 604, SRMs 32 are provided at each of discrete spaced locations of a support, such as support 522. In one implementation, the samples and reagents are mixed prior to dispensing onto support 522. In another implementation, the sample and reagents are sequentially deposited onto each other upon support 522 and each of the discrete spaced locations, wherein mixing of the sample and the reagent occurs on support 522. In one implementation, SRMs 32 are provided at such spaced locations upon support 522 manually using syringes or other manual dispensers. In one implementation, SRMs are provided using a powered actuator, such as applicator 540 and Cartesian robot 545, wherein samples and reagents, already mixed, are deposited onto support 522 by applicator 540 and Cartesian robot 545 or wherein the samples and reagents, not yet mixed, are deposited and mixed on support 522 by applicator 540 and Cartesian robot 545 at each of the discrete spaced locations.

As indicated by block 606, the SRM 32 at each discrete spaced location of support 522 is thermal cycled under the control of controller 550. As indicated by block 610, controller 550 outputs control signals to command heater 530 to heat the sample reagent mixture, SRM 32, at each discrete spaced location. In one implementation in which such thermal cycling is utilized for a polymerase chain reaction, each SRM 32 is heated and maintained at a temperature to facilitate denaturing of SRM 32 during each cycle. In one implementation, each SRM 32 is heated to and maintained at a temperature of at least 90 degrees Celsius and nominally a temperature of 94 degrees Celsius to 98 degrees Celsius for a time period of less than or equal to 0.02 seconds and nominally less than or equal to 0.01 seconds during each cycle.

As indicated by block 614, controller 550 commands Cartesian robot 545 to position applicator 540 across from opposite to each of the discrete spaced locations of support 522 supporting an SRM 32. While applicator 540 is positioned at each discrete spaced location containing SRM 32, controller 550 outputs additional control signals causing applicator 540 to dispense fluid onto the SRM 32 to cool the SRM 32. In one implementation, all of SRMs 32 at the different discrete spaced locations are concurrently heated for block 610 and all of SRMs at the different discrete spaced locations are sequentially cooled through the application of fluid from applicator 540, wherein all of the SRMs 32 undergo a heating and cooling cycle prior to starting a subsequent heating and cooling cycle on any of the SRMs 32.

In another implementation, all of SRMs 32 are grouped into subsets of SRMs, wherein all of the SRM 32 of a particular subset of SRMs undergo a heating cooling cycle prior to starting a subsequent heating and cooling cycle on any of the SRMs of the particular subset. In such an implementation, different subsets of SRMs may undergo heating and cooling cycles at different times. For example, a first subset of the SRMs may be and be undergoing heating pursuant to block 610 while a second different subset of the SRMs may be concurrently undergoing cooling through the sequential application of the fluid to each of the SRM 32 in the second subset pursuant to block 614.

In yet another implementation, a first individual SRM at a first individual spaced location may be undergoing heating pursuant to block 610 while a second individual SRM at a second individual spaced location may be undergoing cooling through the application of the fluid pursuant to block 614. After each individual SRM 32 is heated to the elevated temperature and maintained at the elevated temperature for the predetermined period of time, applicator 540 is positioned with respect to the individual SRM 32 to then apply the fluid to cool the individual SRM 32. Meanwhile, the next successive SRM 32 is being heated, being readied for subsequent cooling by applicator 540.

In one implementation where the thermal cycling method 600 is employed as part of a polymerase chain reaction, controller 550 causes applicator 540 to dispense a fluid at a temperature or multiple temperatures and of sufficient total volume to cool or lower the temperature of SRM to facilitate annealing during an individual cycle. In one implementation, the relative volume and temperature of each SRM 32 and the volume, temperature and number of the droplets of fluid dispensed onto each SRM 32 are such that each SRM 32 experiences a temperature drop from 94 degrees Celsius to 98 degrees Celsius down to 50 degrees Celsius to 65 degrees Celsius. Because the quenching effect induced by dispensed fluid, the temperature drop may occur in fraction of second and even millisecond scale. In one implementation, the temperature drop occurs during a time period of no greater than 2 seconds and nominally no greater than 0.5 seconds.

In one implementation, a single droplet of fluid is dispensed onto each SRM 32 during each cycle. In another implementation, multiple droplets of fluid are dispensed onto each SRM 32 during each cycle. In one implementation, the fluid being dispensed is at a temperature of less than or equal to 40° C. In implementations where multiple droplets are dispensed during a cycle, the temperature of each of the droplets is uniform or the same. In other implementations, the temperature of each of the drop is dispensed during a single cycle may be controlled so as to vary with respect to one another during the individual cycle. In some implementations, the temperature of the drops dispensed may vary from cycle to cycle during the thermal cycling.

In one example implementation, each SRM 32 has a volume of less than or equal to 200 pico liters. In one implementation, each SRM 32 has a volume of 100 to 200 pico liters, and nominally from 160 pico liters to 170 pico liters. At the beginning of each cycle during thermal cycling, each SRM 32 is at a temperature of at least 94 degrees Celsius to 98 degrees Celsius prior to receiving a droplet or multiple droplets of fluid from applicator 540. In such an implementation, controller 550 outputs control signals such that actuator 540, a bubble jet fluid dispenser, jets or otherwise dispenses five droplets onto each SRM 32, each of the droplets of the fluid having a temperature less than the temperature of each SRM 32. In one implementation, each of the droplets are at the same temperature of between 35 degrees Celsius and 40 degrees Celsius. In one implementation, each droplet has a volume of between 20 and 40 pico liters, and nominally 30 pico liters.

As indicated by block 618 and arrow 620, block 610 and block 614 are repeatedly carried out or cycled during thermal cycling until a predetermined threshold or a predetermined number of cycles have been achieved. In one implementation, each cycle has a duration of less than or equal to 6 seconds. For example, in one implementation where method 600 is carried out as part of a polymerase chain reaction involving denaturing, annealing and extending steps during each cycle, denaturing may consume less than or equal to two seconds, and in some implementations, less than or equal to 0.01 seconds. Annealing and extending may consume less than or equal to five seconds, in some implementations, less than or equal to 3.5 seconds.

In one implementation, thermal cycling method 600 comprises at least 25 cycles, and in one implementation, at least 30 cycles. In one implementation, method 600 comprises the completion of at least 30 cycles in less than or equal to a total time of two minutes. In one implementation, method 600 completes 30 cycles in less than or equal to 1.6 minutes.

As indicated by block 624, upon completion of thermal cycling, SRM 32 is imaged. In one implementation, each SRM 32 is relocated to opposite to a camera. In another implementation, a camera is positioned opposite to each SRM. The images of each SRM 32 or a selected sample of the total number of SRMs 32 are analyzed to identify characteristics of each of the SRMs 32.

Figure 8:
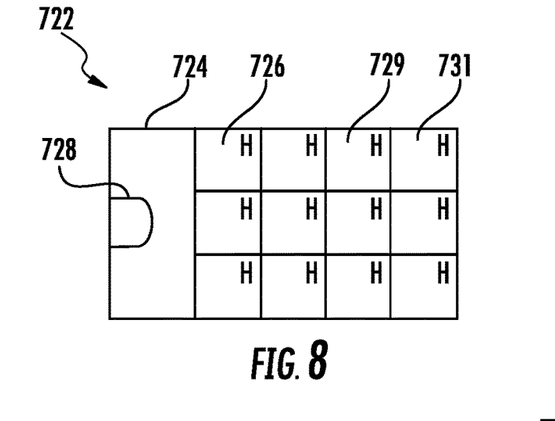
FIG. 8 is a schematic diagram of an example sample reagent mixture (SRM) support.

FIG. 8 is a top view that schematically illustrates an example SRM support 722, an example implementation of an SRM support that may be used to support multiple SRMs 32, such as in system 520 described above. SRM support 722 comprises substrate 724, heaters 726 and electrical connection interface 728. Substrate 724 has an upper surface 729 upon which SRMs 32 may be deposited or formed.

Heaters 726 are each similar to heaters 230 or heater 430 described above. Heaters 726 are carried by substrate 724 at or below the upper surface 729 of support 722. Heaters 726 are provided at each of the plurality of discrete spaced locations 731 of substrate 724. In one implementation, heaters 726 are each independently actuator both to heat an individual SRM at the particular associated location 731. In other implementations, heaters 726 are concurrently commanded to provide uniform heating across surface 729 of support 722. Although support 722 is illustrated as comprising a two-dimensional array or grid of 12 heaters 726 arranged in a 3×4 array, in other implementations, support 722 may comprise a greater or fewer number of such heaters 726 having other arrangements.

Electrical connection interface 728 comprises an interface that facilitates removal connection of the heaters 726 of the support into and out of connection with a controller, such as controller 50 or 550. In one implementation, electrical connection interface 728 comprises an electrically conductive contact pad or multiple electrically conductive contact pads by which support 722 may be plugged into or otherwise removably connected to the controller. In yet another implementation, electrical connection interface 728 comprises a plug or a series of electric conductive pins to be received within corresponding female slots or openings to provide removable a connection to the controller. In still another implementation, electrical connection interface 728 comprises a port having a female receptacle to receive an electrical plug that is in connection with the controller. Electrical connection interface 728 may facilitate the exchange and/or replacement of support 722. Electrical connection interface 728 may facilitate disconnection of support 722 and repositioning of support 722 for imaging, storage or disposal.

Figure 9:
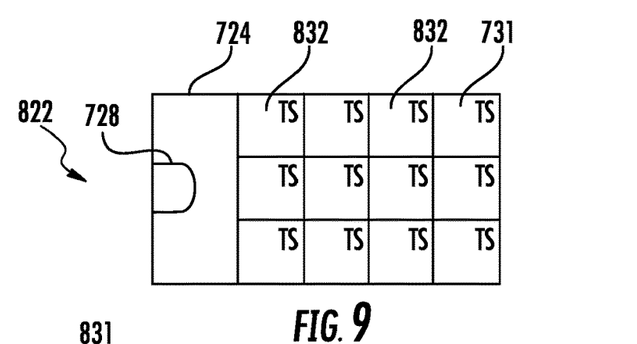
FIG. 9 is a schematic diagram of another example SRM support.

FIG. 9 is a top view schematically illustrates an example SRM support 822, an example implementation of an SRM support that may be used to support multiple SRMs 32, such as in system 520 described above. SRM support 722 comprises substrate 724, electrical connection interface 728 and temperature sensors 832. Substrate 724 and electrical connection interface 728 are described above.

Temperature sensors 832 are carried by substrate 724 at or below the upper surface 729 of support 722. Temperature sensors 832 are provided at each of the plurality of discrete spaced locations 731 of substrate 724. In one implementation, temperature sensors 832 sense a temperature of the associated location 731, facilitating individual feedback and control of the temperature of each of the locations 731 and each of the SRMs supported at each of the location 731. Although support 722 is illustrated as comprising a two-dimensional array or grid of 12 temperature sensors 832 arranged in a 3×4 array, in other implementations, support 722 may comprise a greater or fewer number of such temperature sensors 832 having other arrangements.

Figure 10:
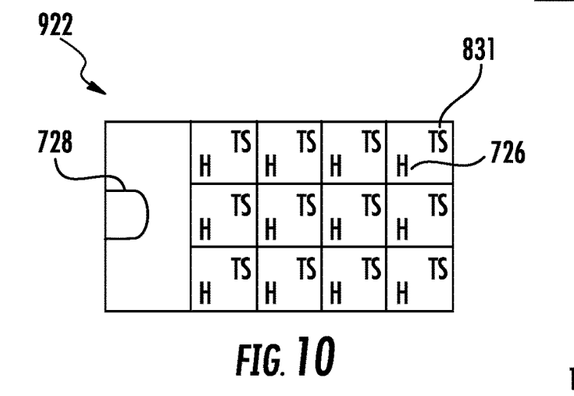
FIG. 10 is a schematic diagram of another example SRM support.

FIG. 10 is a top view schematically illustrates an example SRM support 922, an example implementation of an SRM support that may be used to support multiple SRMs 32 such as in system 520 described above. SRM support 922 comprises substrate 724, heaters 726, electrical connection interface 728 and temperature sensors 832, each of which is described above.

Figure 11:
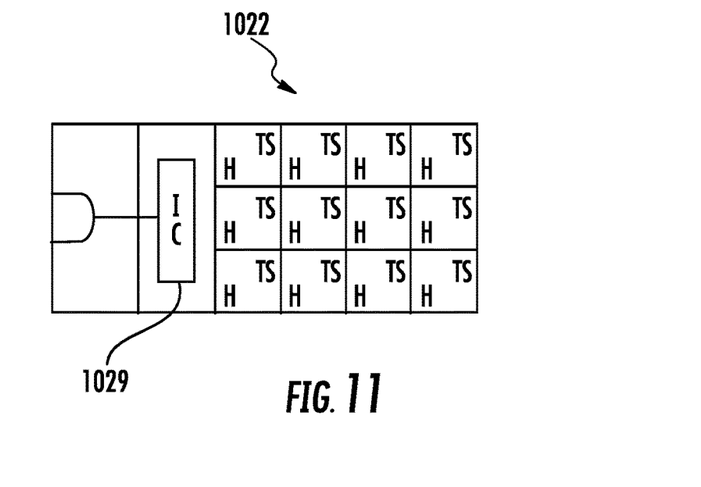
FIG. 11 is a schematic diagram of another example SRM support.

FIG. 11 is a top view schematically illustrates an example SRM support 1022, an example implementation of an SRM support that may be used to support multiple SRMs 32, such as in system 520 described above. SRM support 922 comprises substrate 724, heaters 726, electrical connection interface 728 and temperature sensors 832, each of which is described above. As schematically shown by FIG. 11, support 1022 additionally comprises an onboard integrated circuit 1029. Integrated circuit 1029 facilitates the input and output of signals to heaters 726 and temperature sensors 832, making it easier to plug or connect support 1022 to the external controller. In one implementation, integrate circuit 1029 comprises "dumb" circuits, wherein the "smart" circuits are provided on the external controller. In one implementation, integrated circuit 1029 comprises a field programmable gate array (FPGA) circuit. In other implementations, integrate circuit 1029 may comprise other on board electronics or integrated circuitry.

Figure 12:
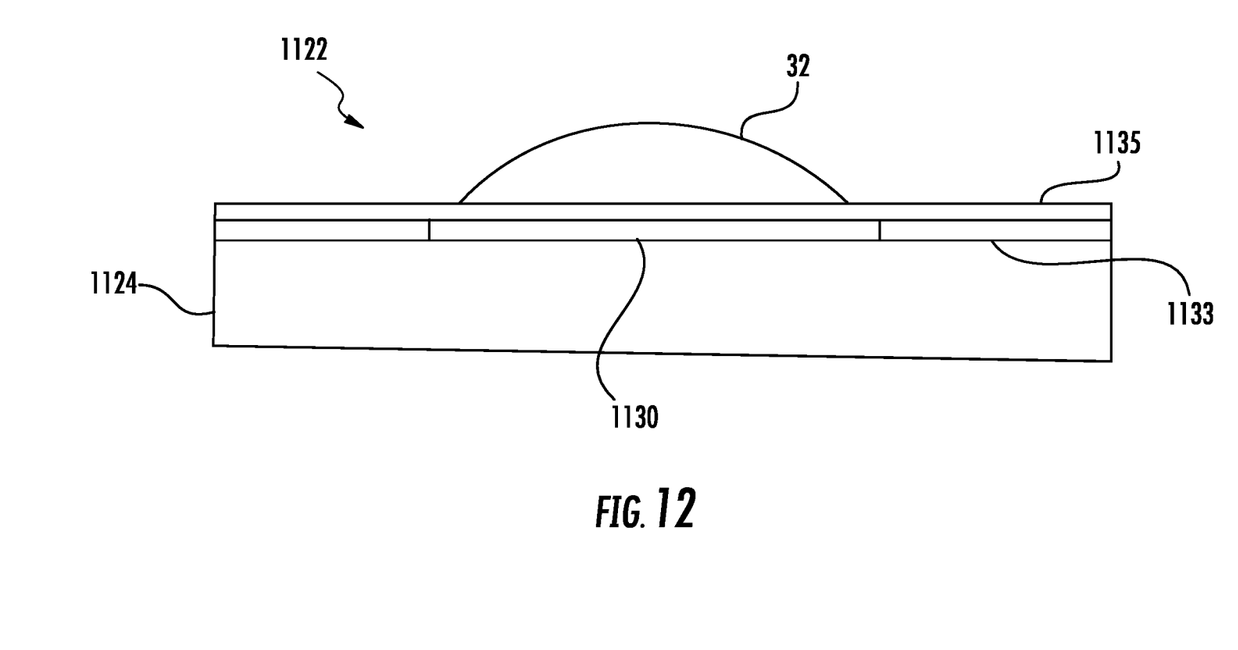
FIG. 12 is a sectional view of a portion of another example SRM support.

FIG. 12 is a sectional view schematically illustrating a portion of an example SRM support 1122 which may be employed as part of system 20, system 520 or other thermal cycling systems. SRM support 1122 comprises substrate 1124, heater/sensor 1130 and electrical trace 1133 and passivation layer 1135. Substrate 1124 comprises a layer of a high dielectric material such as glass, a polymer or silicon.

Heater/sensor 1130 comprises a structure that directs heat to the overlying SRM 32 while also sensing the temperature of SRM 32 for closed loop feedback control of the temperature of SRM 32. In one implementation, heater/sensor 1130 comprises an electrical resistor which generates in amid heat in response to an applied electrical current. In one implementation, the electric resistance of the resistor varies in proportion to temperature, facilitating determination of the temperature of SRM 32 based upon a sensed extend of resistance or elect to current flow through the resistor. In the example illustrated, electrical current is supplied through electroconductive trace 1133. Passivation layer 1135 comprises a layer of dielectric material, such as silicon nitride or silicon carbide that covers heater/sensor 1130 and trace 1133. The above-described construction may be applied to each of multiple distinct regions of support 1122.

In one implementation, support 1122 is formed from, or comprises, materials such that SRM 32 may be imaged through support 1122, similar to support 422 described above. In such an implementation, substrate 1124 is formed from, or comprises, a transparent glass flexible substrate material. In such an implementation, heater/sensor 1130 and electrically conductive trace 1133 are formed from, or comprises, transparent materials such as indium tin oxide. In such an implementation, passivation layer 1135 is further formed from, or comprises, a transparent material, such as silicon carbide or silicon nitride, at least in regions underlying SRM 32.

Figures 13, 14:
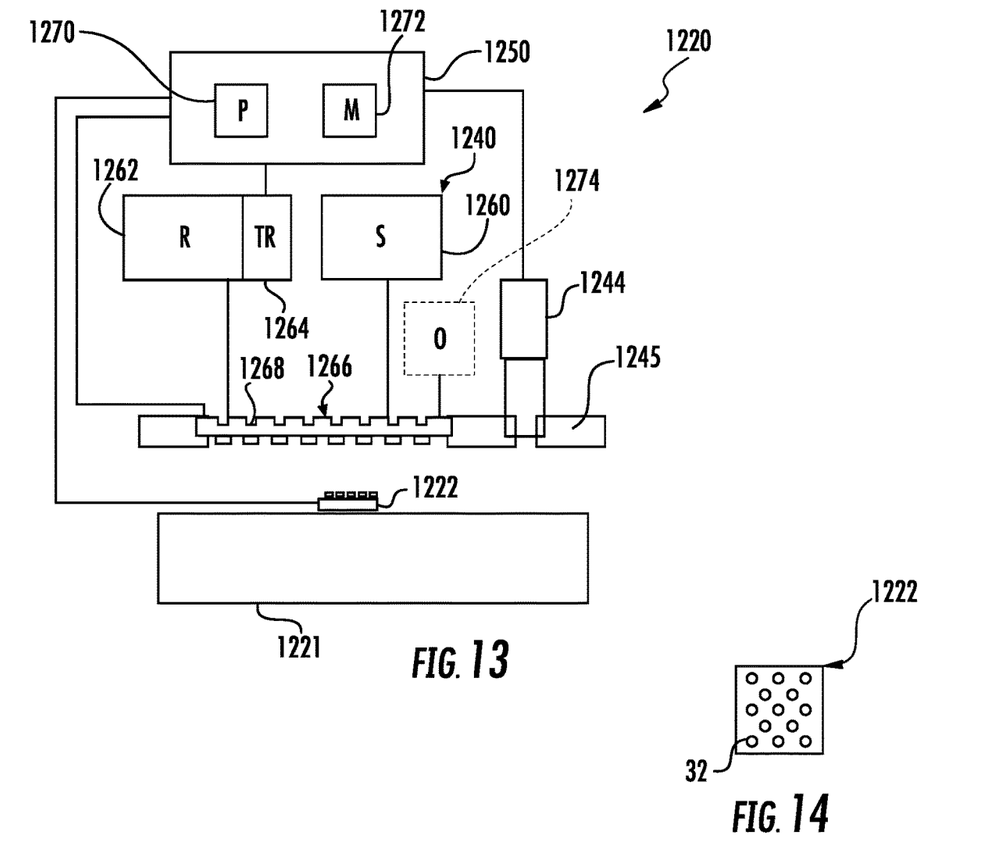
FIG. 13 is a schematic diagram of an example thermal cycling and imaging system.
FIG. 14 is a top view of an example SRM support.

FIG. 13 schematically illustrates thermal cycling and imaging system 1220. System 1220 comprises platform 1221, SRM support 1222, applicator 1240, imager 1244, Cartesian robot 1245 and controller 1250. Platform 1221 comprises a structure for positioning and supporting SRM support 1222. In one implementation, platform 1221 comprises structures or surfaces for aligning, locating and retaining support 1222 in a predefined location relative to robot 1245 and the supported applicator 1240 and imager 1244 to facilitate precise application of SRMs 32 and cooling reagents upon support 1222 and to facilitate imaging of the thermal cycled SRMs. Although platform 1221 is illustrated as supporting a single support 1222, in other implementations, platform 1221 may locate and retain multiple supports 1222.

SRM support 1222 is similar to SRM support 1122 described above except, as shown by FIG. 14, SRM support 1222 supports a multitude of SRMs 32. In the example illustrated, SRM support 1222 supports a two dimensional array or grid of SRMs 32. In one implementation, each region of support 1222 underlying an SRM 32 has a structure similar to that shown in FIG. 12. Each region of SRM support 1222 comprises a heater/sensor 1130 supplied with power through a conductor 1133, wherein the heater/sensor 1130 and conductor 1133 are separated from the SRM 32 by passivation layer 1135 (each of which is shown in FIG. 12).

Applicator 1240 comprises a device that dispenses SRMs 32 on SRM support 1222 and that further dispenses a fluid onto each SRM 32 upon support 1222, wherein the fluid is at a temperature lower than the temperature of the SRM 32 at the time that the SRM 32 is to receive the fluid. In the example illustrated, applicator 1240 comprises sample supply 1260, reagent supply 1262, temperature regulator 1264 and dispenser 1266. Sample supply 1260 comprises a supply of the sample. Reagent supply 1262 comprises a supply of a reagent for being mixed with the sample. In one implementation, supplies 1260, 1262 comprise onboard fluid supplies, such as a cartridge or chamber, carried and moved by robot 1245. In yet another implementation, supplies 1260, 1262 comprise remote or "off-axis" fluid supplies or sources that are remote with respect to dispenser 1266 and robot 1245, wherein fluid is to be supplied to dispenser 1266 across conduits.

Temperature regulator 1264 comprises a device that controls or regulates the temperature of the reagent 1262 being supplied to dispenser 1266. In one implementation, temperature regulator 1264 senses the temperature of reagent in supply 1262, as it is being directed from supply 1262 to dispenser 1266, while it resides within dispenser 1266 and/or as it is being dispensed from dispenser 1266. Temperature regular 1264 further comprises a heating and/or cooling element that may be selectively commanded to heat or cool reagent. In one implementation, temperature regulator 1264 comprises an onboard circuit or controller that automatically commands the heating and/or cooling element based upon the sensed temperature of the reagent such that the reagent being dispensed by dispenser 1266 is at a predefined temperature or within a predefined temperature range. In other implementations, controller 1250 provides such control signals to command the heating and/or cooling element based upon the sensed temperature.

In some implementations, temperature regular 1264 may omit the heating and/or cooling elements, wherein the reagent is at room temperature ambient temperature and wherein an extent to which each SRM 32 is cooled during each thermal cycle is controlled by controlling or varying the volume of reagent, at ambient or room temperature, that is applied to each SRM 32. In some implementations, temperature regulator 1264 may be omitted, wherein the extent to which each SRM is cooled during each thermal cycle is controlled by controlling or varying the volume of the reagent, at ambient room temperature, that is applied to each SRM 32 based upon temperature data received from the heater/sensor 1130 of support 1222.

Dispenser 1266 comprises a device that selectively dispenses a stream or droplets of fluid onto support 1222. In one implementation, dispenser 1266 comprises a plurality of individual dispensing elements 1268 (schematically shown), such as a row of dispensing elements or a two dimensional array of dispensing elements. In one implementation, a first portion of the dispensing elements 1268 dispenses the sample while a second different portion of the dispensing elements 1268 dispenses the reagent. In yet other implementations, each of the dispensing elements 1268 may be selectively utilized to dispense either of the sample or the reagent, wherein applicator 1240 comprises a valve or other flow control mechanism that selectively (a) connects sample supply 1260 to the dispensing element 1268 while reagent supply 1262 is disconnected from the dispensing element 1268, (b) connects reagent supply 1262 to the dispensing element 1268 while sample supply 1260 is disconnected from the dispensing element 1268 or (c) connects both the sample supply 1260 and the reagent supply 1262 to the dispensing element (such as when SRM 32 is being deposited upon support 1222).

In one implementation, each dispensing element 1268 of dispenser 1266 comprises a device that forcefully dispenses the drops of fluid, such as by jetting the drops of fluid, wherein the forcefully dispensed drops of the fluid additionally stir or mix SRM 32 during thermal cycling. In one implementation, each dispensing element 1268 comprises a piezo resistive firing element, wherein electrical current causes deflection of a diaphragm or membrane to forcefully expel the fluid through a nozzle or other opening. In another implementation, each dispensing element 1268 thermal resistive or bubble jet firing element, wherein electrical current is directed across a resistor to vaporize adjacent fluid and create a bubble that forcefully expels adjacent fluid through nozzle or other opening. In one implementation, applicator 40 comprises a bubble jet print head. In yet other implementations, each dispensing on 1268 comprises other fluid ejection or controlled volume fluid dispensing elements.

Imager 1244 comprises a device to output signals based upon captured images of SRMs 32 upon support from 1222. In one implementation, imager 1244 comprises a camera. In the example illustrated, imager 1244 is carried by the Cartesian robot 1245. In other implementations, imager 1244 may comprise mirrors and/or lenses carried by robot 1245, wherein the mirrors and/or lenses focus and direct light reflected off of each SRM 32 during imaging to an image sensing element or multiple image sensing elements that are supported independent of robot 1245.

Cartesian robot 1245, also sometimes referred to as an x-y scanning platform or a gantry robot, comprises a device that selectively repositions applicator 1240 relative to platform 1221 and SRM support 1222. Cartesian robot 1245 facilitates controlled positioning of applicator 1240 such that fluid may be dispensed by applicator 1240 at each of the plurality of distinct, discrete spaced locations of support 1222 containing an individual SRM 32.

Controller 1250 comprises a device that controls the heater/sensors 1130 of support 1222, applicator 1240 and Cartesian robot 1245 to form SRM 32 and to thermal cycle SRMs 32. In one implementation, controller 1250 comprises a processing unit 1270 that follows instructions contained in a non-transitory computer-readable medium 1272, wherein controller 1250 outputs control signals that command heater/sensors 1130, applicator 1240 and Cartesian robot 1245 to thermal cycle SRMs 32.

As shown by broken lines in FIG. 13, in one implementation, applicator 1240 additionally comprises an oil supply 1274 which supplies oil or other evaporation inhibiting fluid to a subset of dispensing elements 1268 of dispenser 1266. In implementations where or supply 1274 is provided, controller 1250 may command dispenser 1266 to dispense a layer of oil, from all supply 1274, on support 1222 prior to the dispensing of the sample in the reagent to form SRM 32. In such an implementation, the sample and reagent are jetted into the oil and onto support 1222. The oil covers and encompasses each SRM puddle upon support 1222 to inhibit evaporation during thermal cycling. In other implementations, oil supply 1274 may be omitted.

Figure 15:
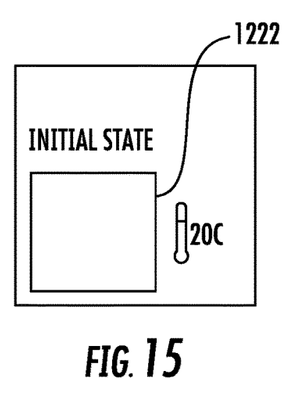
FIG. 15 is a top view of an example SRM support in an initial state.
Figure 16:
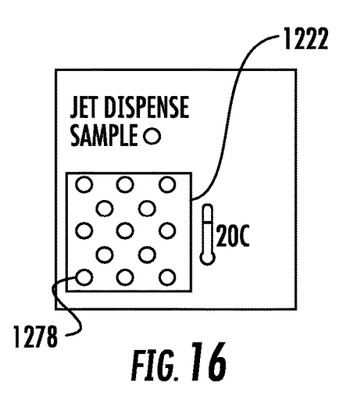
FIG. 16 is a top view of the example SRM support after dispensing of sample depositions onto the support.
Figure 17:
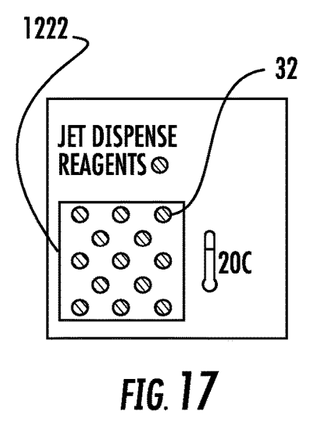
FIG. 17 is a top view of the example SRM support after dispensing of reagents onto the sample depositions to form SRMs.

FIGS. 15-20 illustrate an example method that may be carried out by system 1220. FIGS. 16-20 are top views of SRM support 1222 during SRM formation and thermal cycling. FIGS. 15-17 illustrate the provision of a two dimensional array of SRM 32 on SRM support 1222. FIG. 15 illustrates SRM support 1222 in an initial state prior to the formation of SRM 32. FIG. 16 illustrates SRM support 1222 after the sample from sample supplied 1260 has been deposited at each of a plurality of discrete spaced locations on the surface of support 1222. In the example illustrated, controller 1250 outputs control signals causing Cartesian robot 1245 to appropriately position dispenser 1266 at each of the discrete spaced locations over or opposite to support 1222, wherein at each location, controller 1250 outputs control signals causing dispenser 1266 to dispense the sample, forming a sample deposit 1278 at each of the discrete spaced locations.

FIG. 17 illustrates SRM support 1222 after the reagent from reagent supply 1262 has been applied to each of the sample deposits on support 1222 to form the different SRMs 32. In the example illustrated, controller 1250 outputs control signals causing Cartesian robot 1245 to appropriately position dispenser 1266 at each of the discrete spaced locations over or opposite to support 1222, wherein at each location, controller 1250 outputs control signals causing dispenser 1266 to dispense reagent onto each sample deposit 1278 at each of the discrete spaced locations to form SRMs 32. In implementations where dispenser 1266 forcefully ejects or jets the reagent onto the previously dispensed sample deposits, the reagent is mixed on the surface of support 1222 with the sample to form the SRM 32. In other implementations, the sample and the reagent may be mixed together prior to being deposited upon support 1222 each of the discrete spaced locations.

Figure 21:
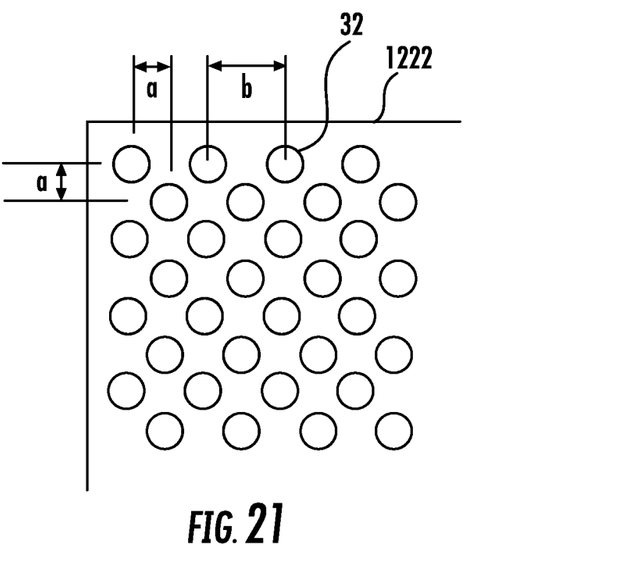
FIG. 21 is a top view of an example SRM support illustrating an example patterning of SRM 32 upon the support.
Figure 22:
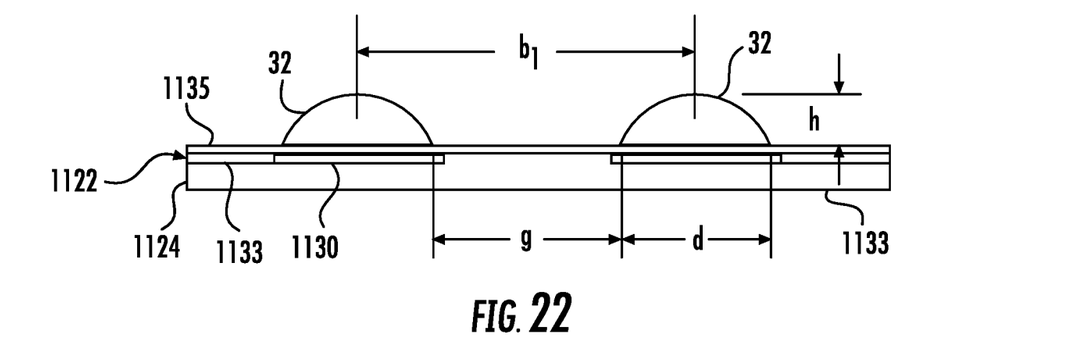
FIG. 22 is a sectional view of a portion of the SRM support of FIG. 21 with the patterned SRMs 32.

FIGS. 21 and 22 illustrate one example layout, pattern or arrangement for the formed SRMs 32 upon support 1222. In the example illustrated, each SRM 32 is deposited as a puddle having the shape of a spherical cap, wherein the individual SRM puddles are arranged in staggered or offset rows to provide interleaved square patterns such that center point of each of the puddles have a spacing distance a. The interleaved square patterns provide a compact arrangement of the SRMs 32.

In one implementation, each of SRMs 32 has a volume of less than or equal to 200 pico liters and nominally 165 pico liters. The small volume of each SRM 32 facilitates quick temperature response, facilitating faster heating and faster cooling during thermal cycling. As shown by FIG. 22, in one implementation, each SRM puddle has a height h and a diameter d. In one implementation, the height h is 35 μm and the diameter d is 102 μm. The center to center spacing distance is less than or equal to 300 and nominally 158 μm. A gap g between consecutive puddles 32 in a row is 121 μm. The example layout provides 9800 SRMs 32 in a square pattern of 22 mm×22 mm, with to 70×70 drop square patterns spaced by 2 a on center. As shown by FIG. 22, in the example illustrated, SRMs 32 have a minimum center distance b between puddles in a row of 223 μm.

Figure 18:
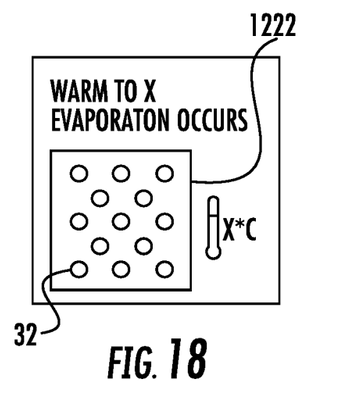
FIG. 18 is a top view of the example SRM support with the SRMs undergoing heating during a cycle.
Figure 19:
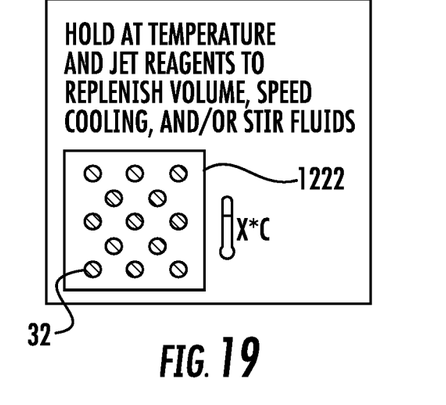
FIG. 19 is a top view of the example SRM support with the SRMs undergoing cooling during the cycle.
Figure 20:
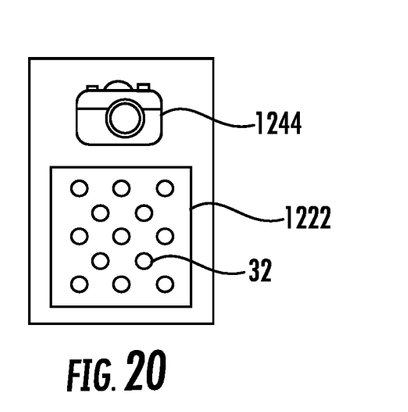
FIG. 20 is a top view of the example SRM support with the thermal cycled SRMs being imaged.

FIGS. 18 and 19 illustrate each SRM 32 undergoing thermal cycling. As illustrated by FIG. 18, controller 1250 outputs control signals to command heater/sensors 1130 to heat each SRM 32 at each discrete spaced location. In one implementation in which such thermal cycling is utilized for a polymerase chain reaction, each SRM 32 is heated and maintained at a temperature to facilitate denaturing of each SRM 32 during each cycle. In one implementation, each SRM 32 is heated to and maintained at a temperature of at least 90 degrees Celsius and nominally a temperature of 94 degrees Celsius to 98 degrees Celsius for a time period of less than or equal to 0.02 seconds and nominally less than or equal to 0.01 seconds during each cycle.

As illustrated by FIG. 13, controller 1250 commands Cartesian robot 1245 to position dispenser 1266 across from opposite to each of the discrete spaced locations of support 1222 supporting an SRM 32. While dispenser 1266 is positioned at each discrete spaced location containing an SRM 32, controller 1250 outputs additional control signals causing dispenser 1266 to dispense reagent from reagent supply 1262 onto the SRM 32 to cool the SRM 32. In one implementation, all of SRMs 32 at the different discrete spaced locations are concurrently heated and all of SRMs at the different discrete spaced locations are sequentially cooled through the application of fluid from dispenser 1266, wherein all of the SRMs 32 undergo a heating and cooling cycle prior to starting a subsequent heating and cooling cycle on any of the SRMs 32.

In another implementation, all of SRMs 32 are grouped into subsets of SRMs, wherein all of the SRM 32 of a particular subset of SRMs undergo a heating cooling cycle prior to starting a subsequent heating and cooling cycle on any of the SRMs of the particular subset. In such an implementation, different subsets of SRMs may undergo heating and cooling cycles at different times. For example, a first subset of the SRMs may be and be undergoing heating pursuant while a second different subset of the SRMs may be concurrently undergoing cooling through the sequential application of the fluid to each of the SRM 32 in the second subset.

In yet another implementation, a first individual SRM at a first individual spaced location may be undergoing heating while a second individual SRM at a second individual spaced location may be undergoing cooling through the application of the fluid. After each individual SRM 32 is heated to the elevated temperature and maintained at the elevated temperature for the predetermined period of time, dispenser 1266 is positioned with respect to the individual SRM 32 to then apply the fluid to cool the individual SRM 32. Meanwhile, the next successive SRM 32 is being heated, being readied for subsequent cooling by dispenser 1266.

In one implementation where the thermal cycling method illustrated in FIGS. 18 and 19 is employed as part of a polymerase chain reaction, controller 1250 causes applicator 1240 to dispense a fluid at a temperature or multiple temperatures and of sufficient total volume to cool or lower the temperature of SRM to facilitate annealing during an individual cycle. In one implementation, the relative volume and temperature of each SRM 32 and the volume, temperature and number of the droplets of fluid dispensed onto each SRM 32 are such that each SRM 32 experiences a temperature drop from 94 degrees Celsius to 98 degrees Celsius down to 50 degrees Celsius to 65 degrees Celsius. In one implementation, the temperature drop occurs during a time period of no greater than 2 seconds and nominally no greater than 0.5 seconds.

In one implementation, a single droplet of fluid is dispensed onto each SRM 32 during each cycle. In another implementation, multiple droplets of fluid are dispensed onto each SRM 32 during each cycle. In one implementation, the fluid being dispensed is at a temperature of less than or equal to 40 degrees Celsius. In implementations where multiple droplets are dispensed during a cycle, the temperature of each of the droplets is uniform or the same. In other implementations, the temperature of each of the drop is dispensed during a single cycle may be controlled so as to vary with respect to one another during the individual cycle. In some implementations, the temperature of the drops dispensed may vary from cycle to cycle during the thermal cycling.

In one example implementation, each SRM 32 has a volume of less than or equal to 200 pico liters. In one implementation, each SRM 32 has a volume of 100 to 200 pico liters, and nominally from 160 pico liters to 170 pico liters. At the beginning of each cycle during thermal cycling, each SRM 32 is at a temperature of at least 94 degrees Celsius to 98 degrees Celsius prior to receiving a droplet or multiple droplets of fluid from applicator 540. In such an implementation, controller 550 outputs control signals such that actuator 540, a bubble jet fluid dispenser, jets or otherwise dispenses five droplets onto each SRM 32, each of the droplets of the fluid having a temperature less than the temperature of each SRM 32. In one implementation, each of the droplet is at a uniform temperature of between 35 degrees Celsius and 40 degrees Celsius. In one implementation, each droplet has a volume of between 20 and 40 pico liters, and nominally 30 pico liters.

In one implementation, the volume of each of the cooling drops of reagent being applied is sufficient to replenish evaporation occurring during the heating of each SRM. In one implementation, each SRM has a nominal volume of 167 pl with a footprint diameter of 102 um and a height of 35 um. For this particular SRM, each urn of fluid lost from its outer surface to evaporation may result in 11.8 pico liters of volume lost. Assuming the vast majority of evaporation occurs during the anneal and extend stages, evaporation may occur at a rate of 4 µm/s, totaling 12.4 µm during the 3.1 seconds of annealing and extending in each cycle. At 12.4 µm per cycle multiplied by 11.8 pico liters per micrometer, the result is a replenishment of 146 pico liters required per cycle. In one implementation, during each cycle 30 pico liters drops are applied to each SRM, the drops being delivered in five passes of dispenser 1266 with one drop of reagent per puddle of SRM per pass. As a result, the 146 pico liters per cycle lost to evaporation during each cycle is replenished by the dispensed reagent during each cycle.

The heating cooling illustrated in FIGS. 18 and 19 is repeatedly carried out or cycled during thermal cycling until a predetermined threshold or a predetermined number of cycles have been achieved. In one implementation, each cycle has a duration of less than or equal to six seconds. For example, in one implementation where such thermal cycling is carried out as part of a polymerase chain reaction involving denaturing, annealing and extending steps during each cycle, denaturing may consume less than or equal to two seconds, and in some implementations, less than or equal to 0.01 seconds. Annealing and extending may consume less than or equal to five seconds, in some implementations, less than or equal to 3.5 seconds.

Figure 23:
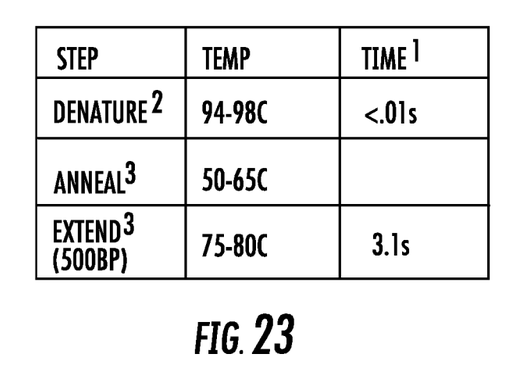
FIG. 23 is a chart illustrating an example thermal cycle of an example polymerase chain reaction.
Figure 24:
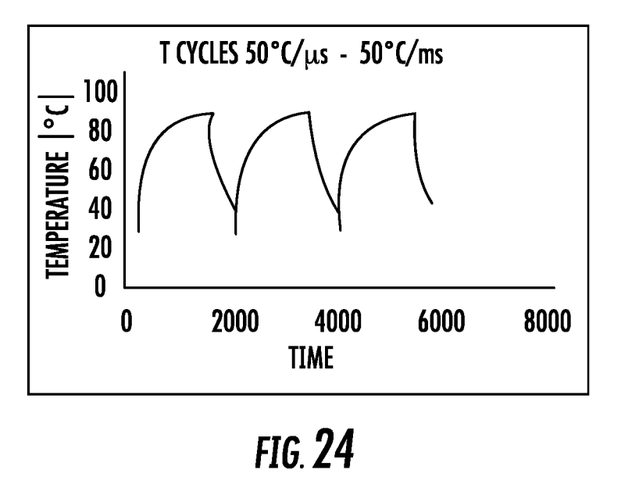
FIG. 24 is a time-temperature graph illustrating example thermal cycles of an example polymerase chain reaction.

FIGS. 23 and 24 provide information regarding the characteristics of one example thermal cycling method for a polymerase chain reaction. As shown by FIG. 23, during denaturing shown in FIG. 18, each are SRM is heated to a temperature of between 94 degrees Celsius and 98 degrees Celsius. Such heating consumes less than 0.01 seconds. During annealing as shown in FIG. 19, each SRM undergoes cooling to a temperature of between degrees Celsius and degrees Celsius. During an extension, each SRM is at a temperature of degrees Celsius to degrees Celsius, consuming approximately 3.1 seconds.

FIG. 24 is a time temperature graph illustrating three examples cycles during thermal cycling. As shown by FIG. 24, during each example cycle, the temperature of each SRM is quickly heated to a temperature of between 94 degrees Celsius and 98 degrees Celsius. Thereafter, the temperature of each SRM 32 is quickly cooled are quenched. In contrast to many existing thermal cycling systems which consume three or more minutes for each cycle, system 1220 consumes less than five seconds per cycle.

In one implementation, controller 1250 carries out the heating and cooling shown in FIGS. 18 and 19 for at least 25 cycles, and in one implementation, at least 30 cycles. In one implementation, system 1220 completes at least 30 cycles in less than or equal to a total time of two minutes. In one implementation, system 1220 completes 30 cycles in less than or equal to 1.6 minutes.

As illustrated by FIG. 19, upon completion of thermal cycling, SRM 32 is imaged. In one implementation, controller 1250 outputs control signals to robot 1245 to sequentially position imager 1244 opposite to each SRM 32. The images of each SRM 32 or a selected sample of the total number of SRMs 32 are analyzed to identify characteristics of each of the SRMs 32.

Figure 25:
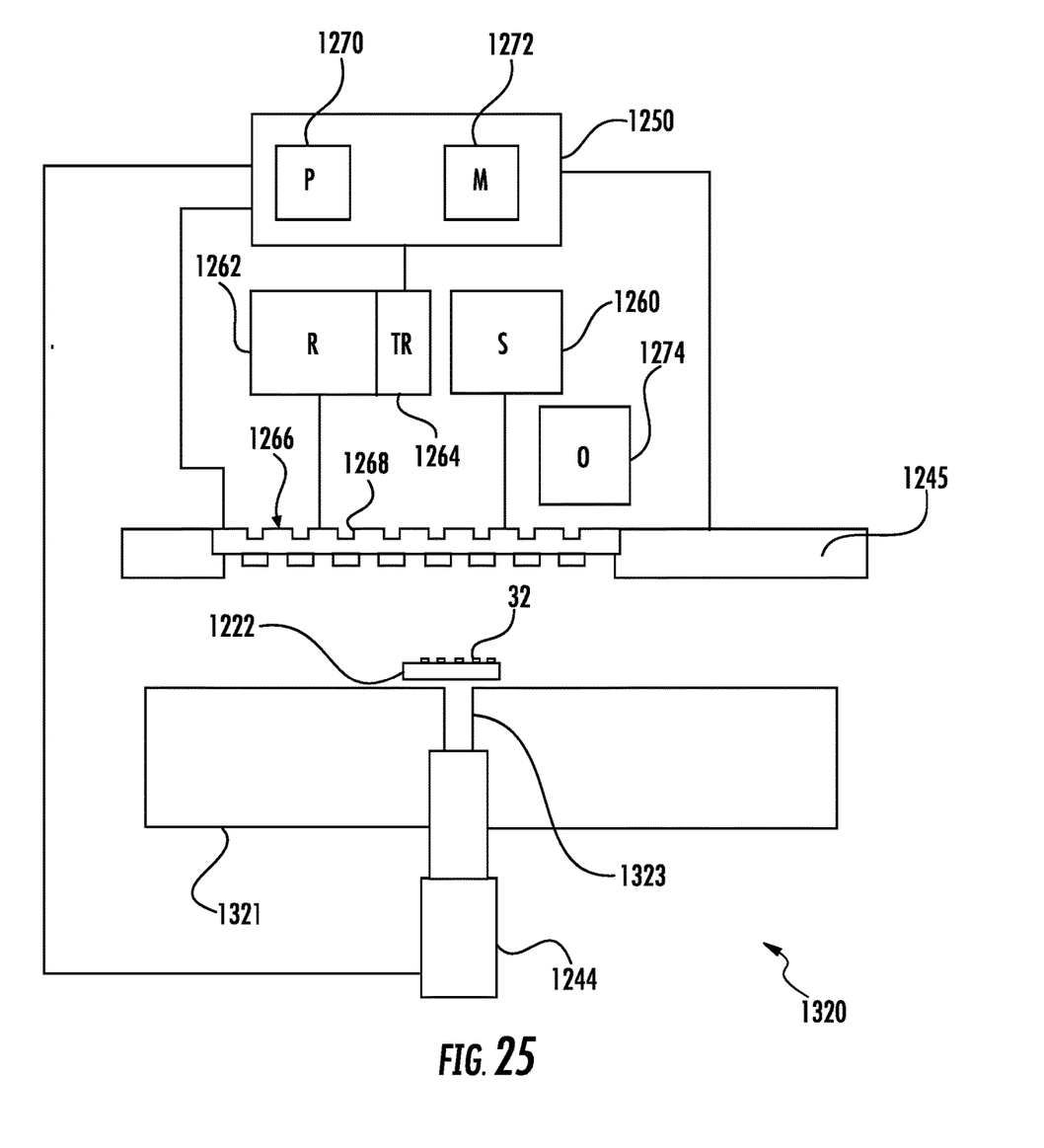
FIG. 25 is a schematic diagram of an example thermal cycling and imaging system.

FIG. 25 schematically illustrates thermal cycling and imaging system 1320. System 1320 is similar to system 1220 except that imager 1244 is positioned beneath SRM support 1222 for imaging SRM 32 after thermal cycling. System 1320 comprises platform 1321, SRM support 1222, applicator 1240, imager 1244, Cartesian robot 1245 and controller 1250. Platform 1321 comprises a structure for positioning and supporting SRM support 1222. In one implementation, platform 1221 comprises structures or surfaces for aligning, locating and retaining support 1222 in a predefined location relative to robot 1245 and the supported applicator 1240 and imager 1244 to facilitate precise application of SRMs 32 and cooling reagents upon support 1222 and to facilitate imaging of the thermal cycled SRMs. Although platform 1221 is illustrated as supporting a single support 1222, in other implementations, platform 1221 may locate and retain multiple supports 1222.

As further shown by FIG. 25, platform 1321 further supports imager 1244. Platform 1321 is similar to platform 1221 described above except that platform 1321 comprises an opening or a transparent portion 1323 beneath or opposite to SRM support 1222. Imager 1244 captures images of the thermal cycled SRMs 32 upon support 1222 through the opening or transparent portion 1323. In such an implementation, SRM support 1222 is formed from, or comprises, a transparent glass or substrate material. In such an implementation, heater/sensor 1130 and electrically conductive trace 1133 are formed from, or comprise, transparent materials such as indium tin oxide. In such an implementation, passivation layer 1135 is further formed from, or comprises, a transparent material, such as silicon carbide or silicon nitride, at least in regions underlying SRM 32.

Although the present disclosure has been described with reference to example implementations, workers skilled in the art will recognize that changes may be made in form and detail without departing from the spirit and scope of the claimed subject matter. For example, although different example implementations may have been described as including one or more features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. An apparatus comprising:
a heater;
a fluid applicator; and
a controller programmed to output control signals to thermal cycle a sample-reagent mixture through a plurality of cycles, each cycle comprising:
outputting control signals actuating the heater to heat the sample-reagent mixture; and
outputting control signals actuating the fluid applicator to dispense a fluid onto the sample-reagent mixture, wherein the fluid has a temperature that is lower than a temperature of the sample-reagent mixture to cool the sample reagent mixture during each cycle.

2. The apparatus of claim 1, wherein the fluid applicator comprises a fluid jetting head.

3. The apparatus of claim 1 further comprising a sample-reagent mixture support to underlie the sample-reagent mixture, wherein the heater is carried by the support.

4. The apparatus of claim 1 further comprising a Cartesian robot coupled to the applicator, wherein the controller is to output control signals actuating the applicator and the Cartesian robot to dispense the fluid onto the sample-reagent mixture at each of discrete spaced locations to cool the sample reagent mixture at each of the discrete spaced locations.

5. The apparatus of claim 4 further comprising an imager carried by the Cartesian robot, wherein the controller is to:
output control signals to the Cartesian robot causing the imager to be positioned with respect to the sample reagent mixture at each of the discrete spaced locations; and
output control signals to the imager causing the imager to image the sample reagent mixture at each of the discrete spaced locations.

6. The apparatus of claim 1 further comprising:
a sample-reagent mixture support to underlie the sample-reagent mixture; and
a Cartesian robot to be coupled to the support, wherein the controller is to output control signals actuating the support and the Cartesian robot to dispense the fluid onto the sample-reagent mixture at each of discrete spaced locations to cool the sample reagent mixture at each of the discrete spaced locations.

7. The apparatus of claim 6 further comprising:
an imager, wherein the imager is carried by the Cartesian robot and wherein the controller is to:
output control signals to the Cartesian robot causing the imager to be positioned with respect to the sample reagent mixture at each of discrete spaced locations; and
output control signals to the imager causing the imager to image the sample reagent mixture at each of the discrete spaced locations.

8. The apparatus of claim 1 further comprising:
a sample-reagent mixture support to underlie the sample-reagent mixture;
an imager to image the sample-reagent mixture through the support.

9. The apparatus of claim 1 further comprising:
a sample-reagent mixture support to underlie the sample-reagent mixture; and
a temperature sensor carried by the support to sense a temperature of the sample reagent mixture upon the support.

10. The apparatus of claim 1, wherein:
the fluid applicator is configured to dispense a fluid onto the sample-reagent mixture; and
the control signals actuating the fluid applicator are further to actuate the fluid applicator to replenish the sample-reagent mixture lost to evaporation.

11. A method comprising:
thermal cycling a sample-reagent mixture through a plurality of cycles, each cycle comprising:
a controller actuating a heater to heat the sample-reagent mixture; and
dispensing a fluid onto the sample-reagent mixture using a fluid applicator as controlled by the controller, wherein the fluid has a temperature that is lower than a temperature of the sample-reagent mixture to cool the sample reagent mixture during each cycle; and
after the thermal cycling, imaging the sample-reagent mixture.

12. The method of claim 11, wherein each cycle has a duration of less than or equal to 6 seconds.

13. The method of claim 11, wherein the sample reagent mixture has a volume of less than or equal to 200 picoliters.

14. The method of claim 11, wherein the plurality of cycles comprises at least 25 cycles.

* * * * *